(12) United States Patent
Narayanan et al.

(10) Patent No.: US 11,744,610 B2
(45) Date of Patent: Sep. 5, 2023

(54) ATHERECTOMY SYSTEM

(71) Applicant: BOSTON SCIENTIFIC LIMITED, Hamilton (BM)

(72) Inventors: Nandu Narayanan, Kannur (IN); Akhilan Gupta, Mandsaur (IN); Nithin Prasanth Kp, Thiruvananthapuram (IN); Bastin Francis, Thrissur (IN)

(73) Assignee: Boston Scientific Limited, Hamilton (BM)

( * ) Notice: Subject to any disclaimer, the term of this patent is extended or adjusted under 35 U.S.C. 154(b) by 104 days.

(21) Appl. No.: 17/524,782

(22) Filed: Nov. 12, 2021

(65) Prior Publication Data

US 2022/0061879 A1     Mar. 3, 2022

Related U.S. Application Data

(63) Continuation of application No. 16/234,501, filed on Dec. 27, 2018, now Pat. No. 11,172,956.

(Continued)

(51) Int. Cl.
*H02P 23/14*      (2006.01)
*A61B 17/3207*    (2006.01)
(Continued)

(52) U.S. Cl.
CPC .. *A61B 17/320758* (2013.01); *A61B 17/3207* (2013.01); *A61B 90/06* (2016.02); *A61B 2017/00017* (2013.01); *A61B 2017/00075* (2013.01); *A61B 2017/00119* (2013.01); *A61B 2017/00132* (2013.01);
(Continued)

(58) Field of Classification Search
CPC ........ A61B 17/320758; A61B 17/3207; A61B 90/06; A61B 2017/00017; A61B 2090/0811
See application file for complete search history.

(56) References Cited

U.S. PATENT DOCUMENTS 3,623,474 A * 11/1971 Heilman ........... A61M 5/14546
                                                                            600/432
5,135,483 A     8/1992 Wagner et al.
(Continued)

OTHER PUBLICATIONS

International Search Report and Written Opinion dated Apr. 2, 2019 for International Application No. PCT/US2018/067764.

*Primary Examiner* — Muhammad S Islam
(74) *Attorney, Agent, or Firm* — Seager, Tufte & Wickhem LLP

(57) ABSTRACT

Medical systems and methods for making and using medical systems are disclosed. Example medical systems may include an atherectomy system configured to engage and remove plaque from walls in vessels of a vascular system. The atherectomy system may include a drive shaft, a rotational tip coupled to an end of the drive shaft, a drive mechanism coupled to the drive shaft to rotate the rotational tip, and a control unit configured to control operation of the drive mechanism. In some cases, the control unit may include a controller for controlling operation of the drive mechanism based on sensed positions of the drive mechanism. The controller may be configured to send data to a host for analysis, compensate a control signal based on a mode of operation of the drive mechanism, determine if a stall is predicted to occur, and/or perform one or more other functions.

20 Claims, 6 Drawing Sheets

Related U.S. Application Data

(60) Provisional application No. 62/613,016, filed on Jan. 2, 2018.

(51) Int. Cl.
  *A61B 90/00* (2016.01)
  *A61B 17/00* (2006.01)

(52) U.S. Cl.
  CPC .............. *A61B 2017/00199* (2013.01); *A61B 2017/00553* (2013.01); *A61B 2090/0811* (2016.02)

(56) References Cited

U.S. PATENT DOCUMENTS

| | | |
|---|---|---|
| 6,039,747 A | 3/2000 | Shturman et al. |
| 9,167,418 B1 | 10/2015 | Tuluca |
| 2003/0120296 A1 | 6/2003 | Shturman et al. |
| 2008/0145817 A1 | 6/2008 | Brennan et al. |
| 2010/0125276 A1 | 5/2010 | Palermo |
| 2015/0127272 A1 | 5/2015 | Sundquist |
| 2016/0015420 A1 | 1/2016 | Higgins et al. |
| 2016/0022307 A1 | 1/2016 | Wasdyke et al. |
| 2016/0030071 A1* | 2/2016 | Ichikawa ........... A61B 18/1445 606/41 |
| 2016/0374716 A1 | 12/2016 | Kessler |

* cited by examiner

ATHERECTOMY SYSTEM

CROSS-REFERENCE TO RELATED APPLICATIONS

This application is a continuation of U.S. patent application Ser. No. 16/234,501 now U.S. Pat. No. 11,172,956, filed Dec. 27, 2018; which claims the benefit of priority under 35 U.S.C. § 119 of U.S. Provisional Application No. 62/613,016, filed Jan. 2, 2018, the entire disclosure of which is hereby incorporated by reference.

TECHNICAL FIELD

The present disclosure pertains to medical devices, and methods for manufacturing and using medical devices. More particularly, the present disclosure pertains to rotational medical devices, methods, and systems, including those with control systems having rotation monitoring and control capabilities.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

BRIEF SUMMARY

This disclosure provides, design, material, manufacturing method, and use alternatives for medical devices and systems. In a first aspect, an atherectomy control system may include a drive mechanism, a position sensor configured to sense a rotational position of the drive mechanism, an input/output port, a microcontroller in communication with the position sensor and the input/output port, and wherein the microcontroller may be configured to determine a speed of the drive mechanism based on received indications of the rotational position of the drive mechanism; and determine a control signal for adjusting the speed of the drive mechanism based on the determined speed of the drive mechanism and output the determined control signal via the input/output port.

In addition or alternative and in a second aspect, the drive mechanism of the control system may be a turbine.

In addition or alternative and in a third aspect, the control system may further include a computing device in communication with the microcontroller and configured to receive the determined speed from the microcontroller, and wherein the computing device may be configured to monitor operation of the drive mechanism based on the determined speed of the drive mechanism received over time.

In addition or alternative and in a fourth aspect, the control system may include data related to the received determined speed of the drive mechanism being password protected at the computing device.

In addition or alternative and in a fifth aspect, the control system may include an is analog-to-digital converter configured to convert analog indications of rotational positions of the drive mechanism to digital indications of the rotational positions of the drive mechanism.

In addition or alternative and in a sixth aspect, the microcontroller may be configured to determine the control signal by comparing the determined speed of the drive mechanism to a speed set point.

In addition or alternative and in a seventh aspect the drive mechanism may have a first mode and a second mode, and the microcontroller may be configured to adjust the determined control signal based on whether the drive mechanism is in the first mode or the second mode.

In addition or alternative and in an eighth aspect, the drive mechanism may operate in the first mode upon start-up and the drive mechanism operates in the second mode starting at a predetermined time after start-up.

In addition or alternative and in a ninth aspect, the microcontroller may be configured to predict a stall of the drive mechanism will occur within a predetermined time period after a current time.

In addition or alternative and in a tenth aspect, the microcontroller may be configured to predict the stall of the drive mechanism will occur within the predetermined time period when a trend value based on the determined speed of the drive mechanism reaches or goes beyond a threshold value.

In addition or alternative and in an eleventh aspect, the trend value may be a difference between a currently determined speed of the drive mechanism and a speed of the drive mechanism at a time that is the predetermined time period before a time at which the currently determined speed of the drive mechanism was taken.

In addition or alternative and in a twelfth aspect, the microcontroller is configured to predict a time until the predicted stall of the drive mechanism will occur.

In addition or alternative and in a thirteenth aspect, a method of controlling a drive mechanism of an atherectomy system using firmware in a microcontroller may include receiving a position indicator of the drive mechanism, determining a speed of the drive mechanism based on the position indicator of the drive mechanism, receiving a set is point for the speed of the drive mechanism, determining a control signal to adjust the speed of the drive mechanism based on the determined speed of the drive mechanism and the received set point for the speed of the drive mechanism, and outputting the determined control signal to adjust the speed of the drive mechanism.

In addition or alternative and in a fourteenth aspect, the method may further include adjusting an initial control signal according to a first mode of operation to determine the control signal during a predetermined time period after startup of the drive mechanism, and adjusting the initial control signal according to a second mode of operation to determine the control signal after the predetermined time period after startup of the drive mechanism has elapsed.

In addition or alternative and in a fifteenth aspect, the method may further include predicting a stall of the drive mechanism will occur within a predetermined time period after a current time.

In addition or alternative and in a sixteenth aspect, the method may further include predicting when a stall of the drive mechanism will occur.

In addition or alternative and in a seventeenth aspect, an atherectomy system may include an advancer assembly configured to operably connect to an elongate member, the advancer assembly configured to control a longitudinal position of the elongate member, the advancer assembly comprising a drive mechanism configured to operably connect to the elongate member and adjust a rotational position of the elongate member, a control console in communication with the advancer assembly, the control console comprising an input/output port and a microcontroller configured to determine a speed of the drive mechanism, determine a control signal for adjusting the speed of the drive mechanism, and output the control signal, via the input/output port, to adjust the speed of the drive mechanism.

In addition or alternative and in an eighteenth aspect, the system may include a computing device in communication with the control console for receiving drive mechanism speed data from the control console, the computing device is configured to monitor operation of the drive mechanism over time based on the received drive mechanism speed data.

In addition or alternative and in a nineteenth aspect, the microcontroller may be configured to identify an initial control signal and adjust the control signal based on whether the drive mechanism is in a startup mode or a steady state mode.

In addition or alternative and in a twentieth aspect, the microcontroller may be configured to determine when a stall of the drive mechanism will occur.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
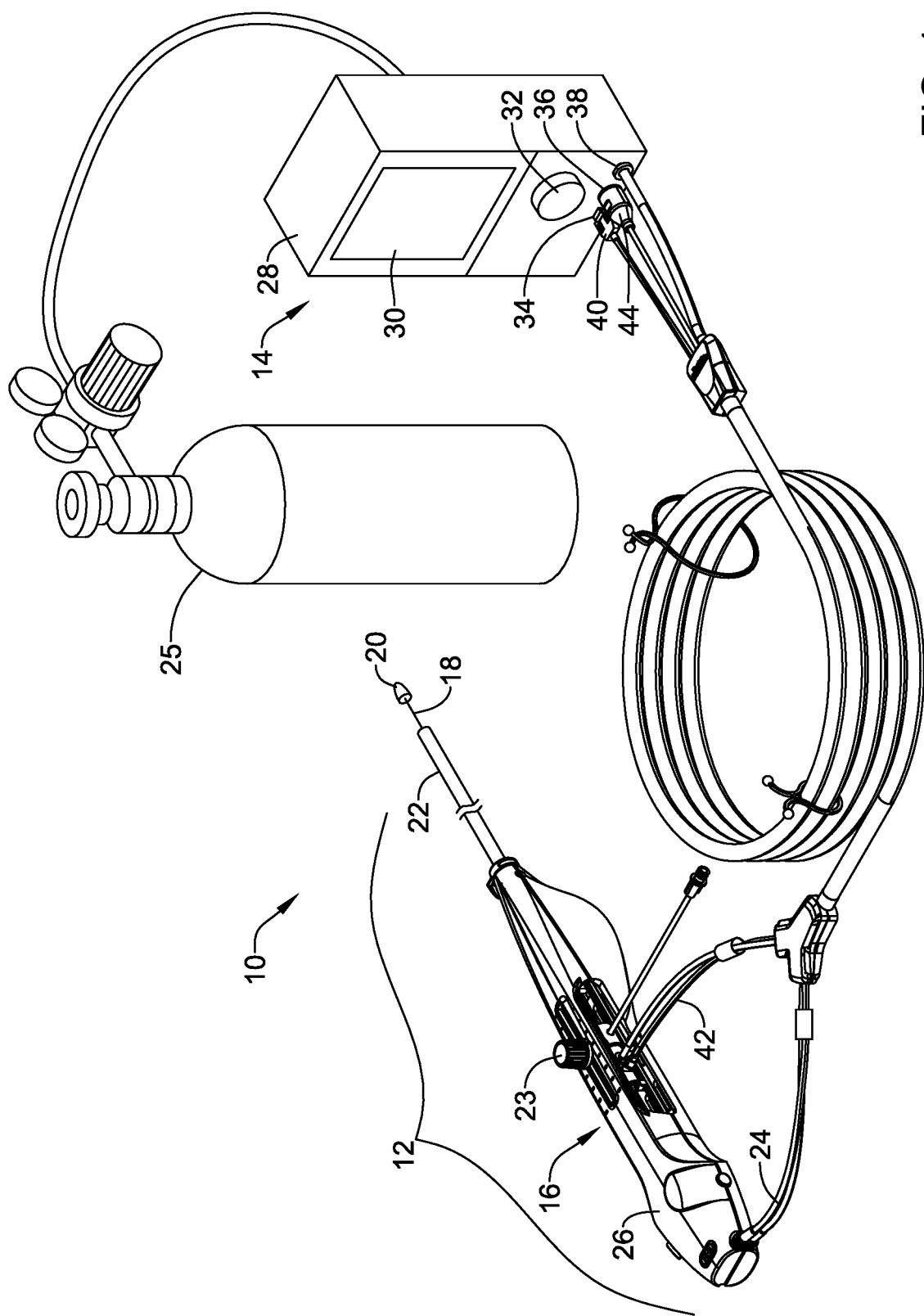
FIG. 1 is a schematic diagram of an example atherectomy system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cardiovascular disease and peripheral arterial disease may arise from accumulation of atheromatous material on the inner walls of vascular lumens, resulting in a condition known as atherosclerosis. Atheromatous and other vascular deposits may restrict blood blow and can cause ischemia in a heart of a patient, vasculature of a patient's legs, a patient's carotid artery, etc. Such ischemia may lead to pain, swelling, wounds that will not heal, amputation, stroke, myocardial infarction, heart attack, and/or is other conditions.

Atheromatous deposits may have widely varying properties, with some deposits being relatively soft and others being fibrous and/or calcified. In the latter case, the deposits may be referred to as plaque. Atherosclerosis occurs naturally as a result of aging, but may also be aggravated by factors such as diet, hypertension, heredity, vascular injury, and the like. Atherosclerosis may be treated in a variety of ways, including drugs, bypass surgery, and/or a variety of catheter-based approaches that may rely on intravascular widening or removal of the atheromatous or other material occluding the blood vessel. Atherectomy is a catheter-based intervention that may be used to treat atherosclerosis.

Atherectomy is an interventional medical procedure performed to restore a flow of blood through a portion of a patient's vasculature that has been blocked by plaque or other material. In an atherectomy procedure, a device on an end of a drive shaft is used to engage and/or remove (e.g., abrade, grind, cut shave, etc.) plaque or other material from a patient's vessel (e.g., artery or vein). In some cases, the device on an end of the drive shaft may be abrasive and/or may otherwise be configured to remove plaque from a vessel wall or other obstruction in a vessel when the device is rotating and engages the plaque or other obstruction.

FIG. 1 depicts an atherectomy system 10. The atherectomy system 10 may include a drive assembly 12 and a control unit 14 (e.g., a controller or control console). Although the drive assembly 12 and the control unit 14 are depicted in FIG. 1 as separate components of the atherectomy system 10, the control unit 14 may be incorporated into drive assembly 12.

The drive assembly 12 may include, among other elements, an advancer assembly 16, a drive shaft 18 (e.g., a flexible drive shaft or other drive shaft), a rotational device 20 (e.g., a rotational tip or other rotational device), and an elongated member 22 having a first end (e.g., a proximal end), a second end (e.g., a distal end), and a lumen extending from the first end to the second end for receiving the drive shaft 18. In some cases, the elongated member 22 may be an elongated tubular member. The rotational device 20 may have a rough or sharp surface, such that it is configured to grind, abrade, cut, shave, etc. plaque from a vessel wall or other obstruction in a vessel when it is rotated.

Figure 2:
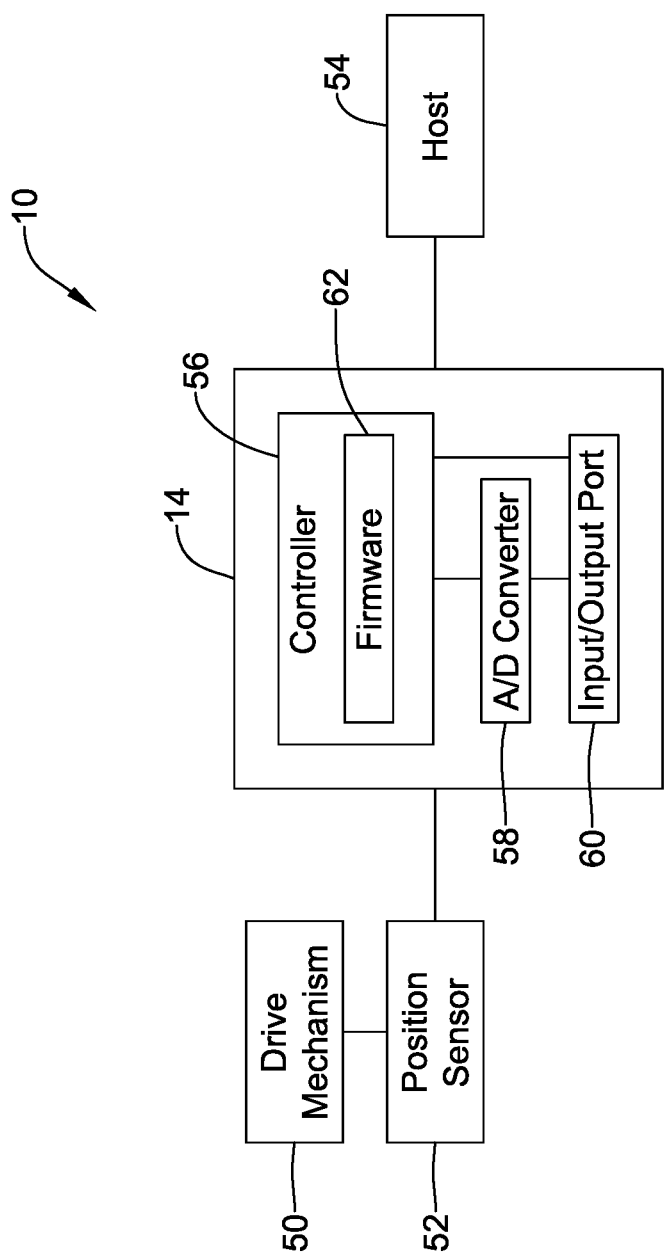
FIG. 2 is a schematic box diagram of an example atherectomy system.

The advancer assembly 16 may include an advancer knob 23 and may house a drive mechanism (e.g., where the drive mechanism is shown in FIG. 2 and may be a turbine, an electric motor, pneumatic motor, and/or one or more other suitable drive mechanisms) in communication with the advancer knob 23 and the drive shaft 18. The advancer knob 23 may be configured to advance along a longitudinal path to longitudinally advance the drive mechanism and the rotational device 20. The drive mechanism may be coupled to the drive shaft 18 in a suitable manner including, but not limited to a weld connection, a clamping connection, an adhesive connection, a threaded connection, and/or other suitable connection configured to withstand high rotational speeds and forces. As the drive shaft 18 may rotate over a wide range of speeds (e.g., at speeds of between zero (0) rotations per minute (RPM) and 250,000 RPM or higher in a clockwise and/or counterclockwise direction), the coupling between the drive mechanism and the drive shaft 18 may be configured to withstand such rotational speed and associated forces.

In some cases, the drive mechanism may be in communication with the control unit 14. When in communication with the control unit 14, the drive mechanism may be in direct communication with the control unit (e.g., directly connected via wiring) or indirect communication (e.g., indirectly connected via multiple wiring connections and/or one or more devices). In one example of indirect communication between a drive mechanism and the control unit 14 may include a drive mechanism (e.g., a turbine or pneumatic motor) powered by compressed air, where the control unit 14 may activate a compressed fluid flow from a cylinder 25 or other component to the drive mechanism (e.g., activate a valve of the control unit 14 or otherwise activate the compressed fluid flow), which may result in rotation of the drive mechanism and the drive shaft 18.

The drive shaft 18 may be formed from one or more of a variety of materials. For example, the drive shaft 18 may be formed from one or more of a variety of materials including steel, stainless steel, and/or other suitable materials.

The drive shaft 18 may have a suitable diameter and/or length for traversing vasculature of a patient. In some cases, the drive shaft 18 may have a diameter in a range from about 0.030 centimeters (cm) or smaller to about 0.150 cm or larger and a working length in a range from about ten (10) cm or shorter to about three hundred (300) cm or longer. Alternatively, the drive shaft 18 may have a different suitable diameter and/or different suitable length.

The rotational device 20 may have an outer perimeter which is equal to or larger than a distal diameter of the drive shaft 18 and the elongated member 22. The rotational device 20 may have a symmetric design so that it penetrates equally well in both rotational directions, but this is not required and the rotational device 20 may be configured to penetrate in only one direction. The diameter of the drive shaft 18 may depend on the dimension of the lumen of the elongated member 22 and/or one or more other factors.

The rotational device 20 may be coupled to the drive shaft 18. Where the drive shaft 18 has a first end portion (e.g., a proximal end portion) and a second end portion (e.g., a distal end portion), the rotational device 20 may be coupled to the drive shaft 18 at or near the second end portion. In some cases, the rotational device 20 may be located at or adjacent a terminal end of the second end portion of the drive shaft 18.

The rotational device 20 may be coupled to the drive shaft 18 in any manner. For example, the rotational device 20 may be coupled to the drive shaft 18 with an adhesive connection, a threaded connection, a weld connection, a clamping connection, and/or other suitable connection configured to withstand high rotational speeds and forces. Similar to as discussed above with respect to the connection between the drive shaft 18 and the drive mechanism, as the drive shaft 18 and/or the rotational device 20 may rotate at speeds between zero (0) RPM and 250,000 RPM or higher in a clockwise and/or counter clockwise direction, the coupling between the drive shaft 18 and the rotational device 20 may be configured to withstand such rotational speeds and associated forces.

The drive assembly 12 and the control unit 14 may be in communication and may be located in or may have a same housing and/or located in or have separate housings (e.g., an advancer assembly housing 26 and a control unit housing 28, respectively, or other housings). Whether in the same housing or in separate housings, the drive assembly 12 and the control unit 14 may be in communication through a wired (e.g., via one or more electrical lines 24) and/or a wireless connection. Wired connections may be made via one or more communication protocols including, but not limited to, USB, Ethernet, SPI, UART, HDMI, and/or any other suitable common or proprietary wired protocol, as desired. Wireless connections may be made via one or more communication protocols including, but not limited to, cellular communication, ZigBee, Bluetooth, WiFi, IrDA, dedicated short range communication (DSRC), EnOcean, and/or any other suitable common or proprietary wireless protocol, as desired.

Although not shown in FIG. 1, the drive assembly 12 may include and/or enclose one or more operational features in addition to those discussed above and/or as alternatives to those discussed above. For example, among other features, the drive assembly 12 may include a start/stop button, rubber feet, mode selection buttons, a mode start/stop button, control electronics, drive circuitry, etc.

The control unit 14, which may be separate from the drive assembly 12 (e.g., as shown in FIG. 1) or may be included in the drive assembly 12, may include several features. For example, as shown in FIG. 1, the control unit 14 may include a display 30 and a control knob 32 (e.g., a drive mechanism speed (e.g., RPM or other speed) adjustment knob or other control knob). Additionally or alternatively, the control unit 14 may include one or more other features for controlling the drive mechanism and/or other features of the drive assembly 12 (e.g., one or more drive mechanism states) including, but not limited to, a processor, memory, input/output devices, a speaker, volume control buttons, on/off power supply switch, drive mechanism activation switch, a timer, a clock, and/or one or more other features.

The display 30 may be or may include any suitable type of display panel using any suitable display panel technology.

For example, the display 30 may include one or more of the following types of display panels: Eidophor, Electroluminescent display (ELD), Electronic paper (E Ink, Gyricon), Light emitting diode display (LED), Cathode ray tube (CRT) (Monoscope), Liquid-crystal display (LCD) (TFT, LED, Blue Phase, IPS), Plasma display panel (PDP) (ALiS), Digital Light Processing (DLP), Liquid crystal on silicon (LCoS), Organic light-emitting diode (OLED) (AMOLED), Organic light-emitting transistor (OLET), Surface-conduction electron-emitter display (SED), Field emission display (FED), Laser TV (Quantum dot, Liquid crystal), MEMS display (IMoD, TMOS, DMS), Quantum dot display (QD-LED), Ferro liquid display (FLD), Thick-film dielectric electroluminescent technology (TDEL), Telescopic pixel display (TPD), Laser Phosphor Display (LPD), or other type of display panel. The display 30 may include a touch sensitive screen for receiving input, but this is not required.

The control knob 32 may be any suitable type of control knob. As depicted in FIG. 1, the control knob 32 may be a physical control knob that is adjusted (e.g., rotated or otherwise translated) to adjust a control feature (e.g., speed of rotation of the drive mechanism or other control feature). Alternatively or in addition, the control knob 32 may be a virtual control knob that may be adjusted by interacting with a touch sensitive surface.

As depicted in FIG. 1, the control unit 14 may include one or more ports including, but not limited to, a fiber optic port 34, an electrical port 36, a fluid port 38, and/or one or more other ports. The fiber optic port 34 may be configured to receive a fiber optic connector 40 of a fiber optic line 42, where the fiber optic line 42 may be connected to and/or may be part of a position sensor configured to optically sense a position of the drive mechanism. Additionally or alternatively, other types of position sensors may be utilized that have different types of connections to the control unit 14. The electrical port 36 may be configured to receive an electrical connector 44 of the electrical line 24, where the electrical line 24 may be connected to and/or may be part of control electronics at the drive assembly 12. In some cases, the electrical line 24 may be directly connected to a main PCB of the drive assembly 12 and may be utilized to power an electrical assembly of the drive assembly 12. The fluid port 38 may be configured to receive a fluid line connector 46 of a fluid line 48, where the fluid line 48 may be in communication with the drive mechanism to power the drive mechanism. In instances when the drive mechanism is an electrical motor or a non-pneumatic drive mechanism, the fluid port 38, the fluid line connector 46, and/or the fluid line 48 may be omitted, but this is not required.

FIG. 2 depicts a schematic box diagram of the atherectomy system 10 having a drive mechanism 50 and position sensor 52 in communication with the control unit 14 and a host 54 in communication with the control unit 14. The host 54 may be one or more of a laptop computer, a desktop computer, tablet computer, a remote server, smartphone, and/or other computing device. The host 54 may be in wired and/or wireless communication with the control unit 14, where the wired or wireless communication may include one or more of the communication protocols discussed herein.

In operation, the position sensor 52 may sense a rotational position of the drive mechanism 50 and send an indication of the sensed rotational position of the drive mechanism 50 to the control unit 14 (e.g., send an optical pulse or other indication over the fiber optic line 42 or other line). The control unit 14 may then use the indications of the sensed rotational position of the drive mechanism 50 to determine a speed (RPMs) of the drive mechanism 50 and output the determined speed of the drive mechanism 50 to the host 54 for monitoring and/or analysis of the drive mechanism 50.

In some cases, the control unit 14 (e.g., firmware therein) may sample speed data (e.g., rotational speed, lateral speed, longitudinal speed, etc.) and/or other data at predetermined intervals and send the data to the host 54. Example predetermined intervals may include, but are not limited to, 1 millisecond (ms), 2 ms, 5 ms, 10 ms, and/or other suitable intervals. Alternatively or in addition, the control unit 14 may sample speed data and/or other data upon request from the host 54 and/or other input requesting data.

The host 54 may be configured to receive data (e.g., operational data that may include, but is not limited to, speed data, on/off data, stall data, data as a function of time, etc.) from the control unit 14. For example, the host 54 may perform analyses on the speed of the drive mechanism 50 and/or other data related to the operation of the drive mechanism 50 and monitor initial overshoot of the drive mechanism (e.g., actual speed versus a setpoint speed upon startup of the drive mechanism), steady state oscillation of the drive mechanism 50, speed changes over run time of the drive mechanism 50, and/or other operations of the drive mechanism 50. In some cases, the host 54 may plot speed versus time on a graph and/or provide other graphical depictions of the received data.

In some cases, the data transmitted from the control unit 14 to the host 54 may be password protected to establish and/or ensure a high level of data security. A password protection protocol may provide one, two, or more levels of data access at the host 54. An example password protection protocol providing two levels of data access may include a read mode for data access and a read/write mode for data access. Read mode may provide read-only access to the data and may allow a user to view data, but not to interact with the data. Read/write mode may provide read-write access to the data and may allow a user to view data and interact with the data (e.g., change the analyses that are run on the data, add notes to the data, change how data is gathered, etc.). In some cases, read mode or access of the password protection protocol may be accessed after entering or providing a primary or base password. Read/write mode may be accessed after entering or providing a primary or base password and a secondary password. Alternatively, a user's password may automatically give them access to either read mode or read/write mode and only a single password is needed. Although not required in all instances, when the password is provided to the host 54 (e.g., via a keyboard, touch screen, biometric sensing, and/or one or more other input interface), the host 54 may be required by the password protocol to complete an initial handshake with the control unit 14 before receiving access to one or both of the read mode and read/write mode.

In one example configuration, the indication of the sensed rotational position of the drive mechanism 50 may be light pulses and the control unit 14 may include components configured to convert the pulses into analog voltage pulses (e.g., analog indications of rotational positions of the drive mechanism 50). The control unit 14 may include a controller 56, an analog-to-digital (A/D) converter 58, and one or more input/output ports 60. The A/D converter 58 may convert the analog voltage pulses to a digital voltage signal (e.g., digital indications of the rotational positions of the drive mechanism 50) and firmware 62 of the controller 56 may be configured to sample voltage from the A/D converter 58 at predetermined intervals or upon request from a computing device (e.g., the host 54). In some cases, the indications of speed from the position sensor 52 and/or the output data to the host 54 may pass through the input/output port 60.

The controller 56 may be or may include a microcontroller. Additionally or alternatively, the controller may include one or more of an application specific integrated circuit (ASIC) and/or an application specific standard product (ASSP). Although not shown, the controller 56 may include a processor and memory, where the processor may be operably coupled to the memory. The memory may be used to store any desired information, such as control algorithms, set points, predetermined time intervals for sampling data, schedules, reference schedules, times, diagnostic limits, such as, for example, speed limits, RPM limits, torque limits, and the like. The memory may include any of one or more suitable types of storage devices including, but not limited to, RAM, ROM, EPROM, flash memory, a hard drive, and/or the like. The memory may include the firmware 62, which may be accessed by the processor. In some cases, the control unit 14 may store information within the memory, and the processor of the controller 56 may subsequently retrieve the stored information from the memory to effect operation of the atherectomy device and/or for analysis (e.g., for analysis by the host 54). The processor and/or the memory may include and/or be in communication with a timer.

Figure 3:
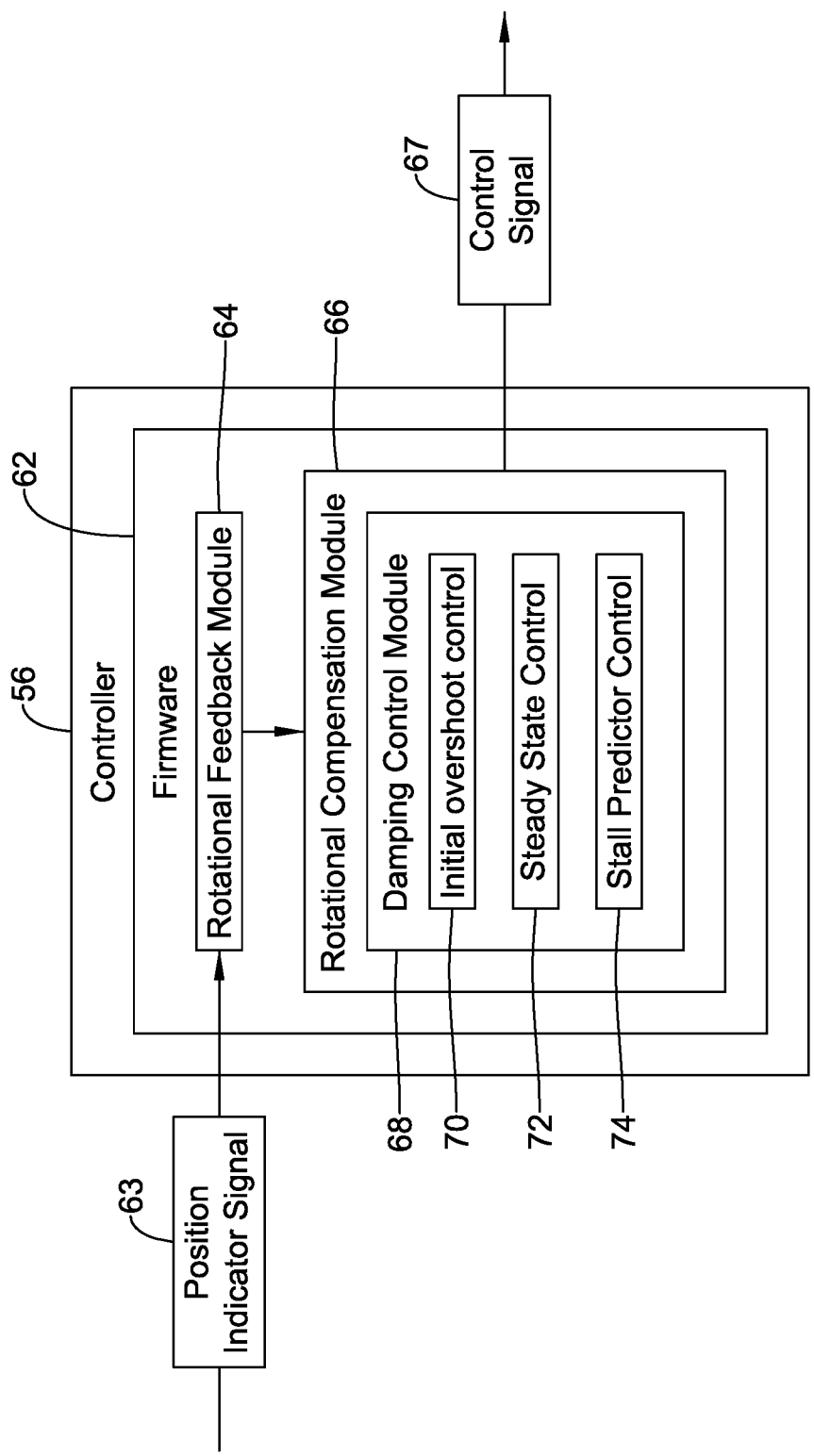
FIG. 3 is a schematic box diagram of an example controller for an atherectomy system.

FIG. 3 depicts a block diagram of the controller 56 and firmware modules in the firmware 62. As depicted in FIG. 3, a position indicator signal 63 for indicating a position of the drive mechanism 50 may be received at the controller 56 and the firmware modules may utilize the position indicator signal 63 to develop control signals 67 for controlling operation (e.g., rotation) of the drive mechanism 50.

The firmware 62 may include a variety of firmware modules. As shown in FIG. 3, the firmware 62 may include a speed feedback module 64, a speed compensation module 66, and a damping control module 68. In some cases, the damping control module 68 may include an initial overshoot control 70, a steady state control 72, a stall predictor control 74, and/or one or more other components. In some cases, one or more of the initial overshoot control 70, the steady state control 72, and the stall predictor control 74 may be separate from the damping control module 68. Alternatively or in addition to the control modules and components depicted in FIG. 3, other firmware modules and/or components may be utilized as desired. The modules 64, 66, 68, of the firmware 62 are describe in greater detail below with respect to the methods of FIGS. 4-6.

Figure 4:
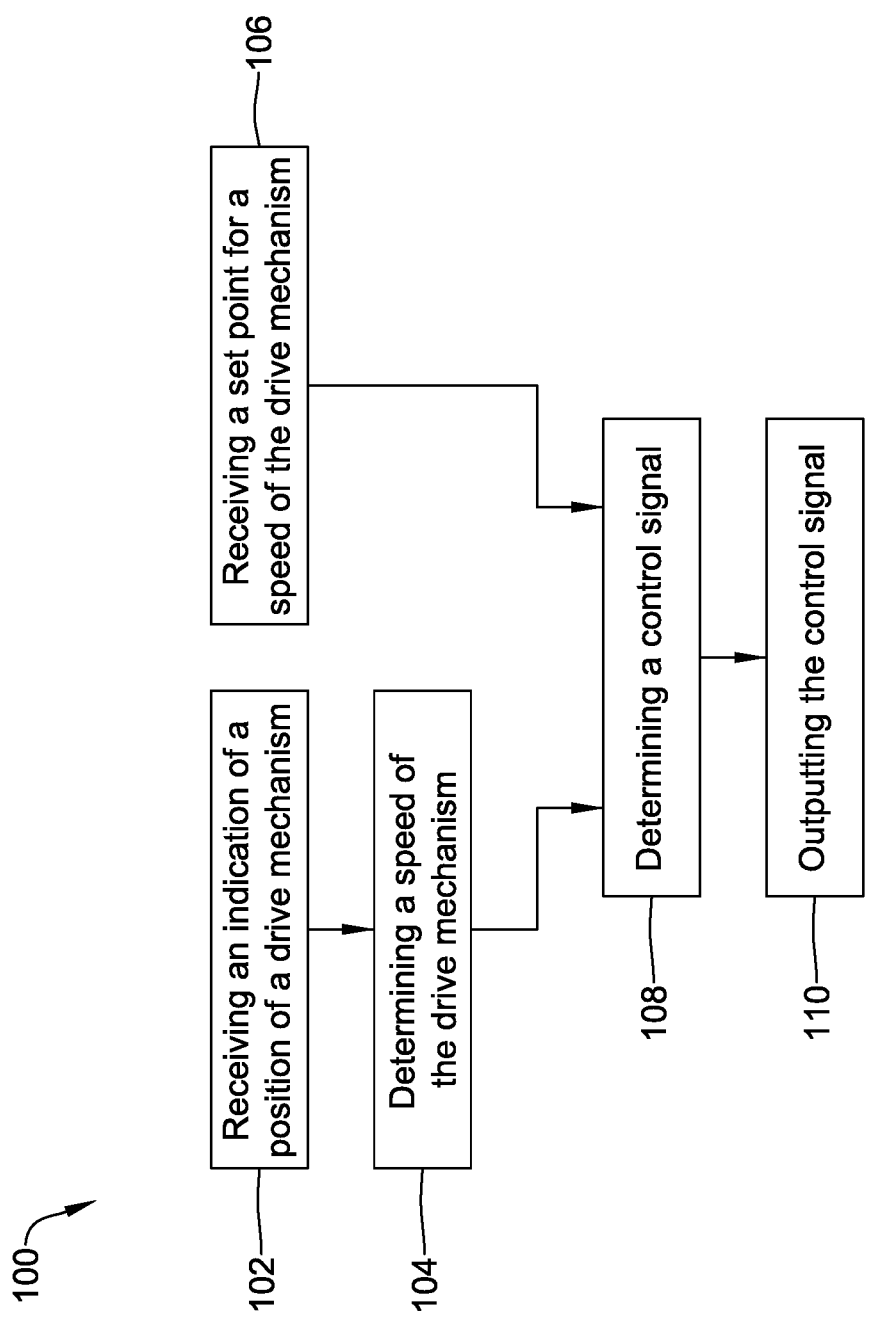
FIG. 4 depicts a schematic flow diagram of an example method of controlling rotation of a drive mechanism of an atherectomy system.
Figure 5:
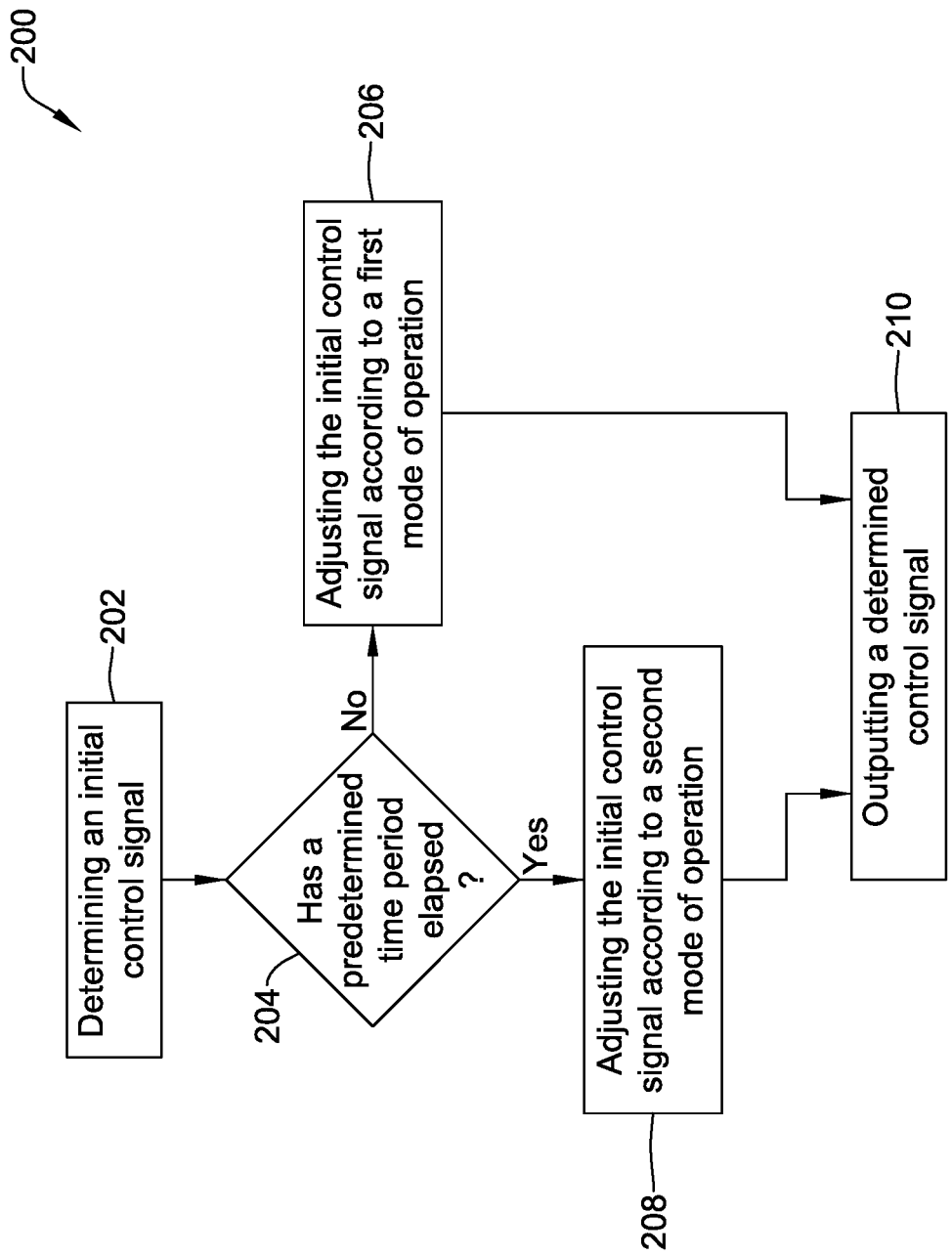
FIG. 5 depicts a schematic flow diagram of an example method of controlling rotation of a drive mechanism of an atherectomy system.

FIG. 4 depicts a method 100 of controlling a speed of the drive mechanism 50. In the method 100, an indication of a position of the drive mechanism 50 may be received 102 (e.g., from the A/D converter 58 and/or other component of the control unit 14) and a speed (e.g., RPM or other measurement of speed) of the drive mechanism 50 may be determined 104. For example, the speed feedback module 64 may be configured to utilize digital indications (e.g., pulses or other indications) of the position of the drive mechanism 50 outputted from the A/D converter 58 to determine a speed (e.g., in RPMs or other measurement of speed) and provide the determined speed to the speed compensation module 66. In such cases, the firmware 62 may store the output from the A/D converter 58 and the speed feedback module 64 may be configured to sample that stored output from the A/D converter 58 to calculate a speed of the drive mechanism 50. Alternatively or in addition, the output from the A/D converter 58 may be provided directly to the speed feedback module 64 for calculating the speed of the drive mechanism 50 and/or for other purposes.

In some cases, the speed feedback module 64 may sample indications of the drive mechanism position (e.g., stored output from the A/D converter 58, direct output from the A/D converter 58, and/or other indications of the drive mechanism position) and determine a speed of the drive mechanism 50 at predetermined intervals. Example predetermined intervals may be ten (10) ms, twenty-five (25) ms, fifty (50) ms, one hundred (100) ms, five hundred (500) ms, second, and/or one or more other suitable intervals. When the indications of the drive mechanism position are pulses, the speed feedback module 64 may determine a number of pulses that occurred during the predetermined interval (e.g., the number of pulses since a last time a sample was taken).

To determine 104 the speed of the drive mechanism 50 from the received indications of the drive mechanism position, the speed feedback module 64 may enter the indications of the drive mechanism position into an equation that is used to calculate the speed of the drive mechanism 50. In one example of when the indications of the drive mechanism position are pulses, the indications of the drive mechanism position are sampled every fifty (50) ms, and the speed is determined in RPM, the following equation may be utilized:

$$RPM = PulseCount_i * 1.2 \quad (1)$$

The term PulseCount is the number of indications of a drive mechanism position (e.g., pulses or other indications) received during a predetermined interval, i. Alternatively, the speed of the drive mechanism 50 may be determined in one or more other suitable manners, which may be dependent on sampling rate (e.g., the predetermined interval or other interval), type of position measurement of the drive mechanism, and/or one or more other factors.

The method 100 of FIG. 4 may include receiving 106 a set point for a speed of the drive mechanism 50 (e.g., via the control knob 32 of the control unit 14 or in another suitable manner) and the calculated speed of the drive mechanism 50 may be compared to the received set point to determine 108 a control signal configured to control a speed of the drive mechanism 50. For example, the calculated RPM or other measurement of speed may be provided to the speed compensation module 66 for comparison to the received set point speed and determining 108 a control signal 67 based on the comparison. When a speed of the drive mechanism 50 is pneumatically controlled, the control signal 67 may be a control signal (e.g., a voltage adjustment control signal or other control signal) to a valve that adjusts fluid provided to power the drive mechanism 50. When a speed of the drive mechanism 50 electrically controlled, the control signal 67 may be a control signal that adjusts an amount of current or voltage to the drive mechanism 50. Further, other suitable types of control signals 67 are contemplated that are generally configured to directly or indirectly affect a speed of the drive mechanism 50.

When speed of the drive mechanism 50 is measured in RPM, the follow equation may be utilized to determine the control signal 67 for adjusting a speed of the drive mechanism 50:

$$\text{Speed Control Signal} = RPM\_Y\_INTERCEPT - GAIN * RPM \quad (2)$$

where:

$$RPM\_Y\_INTERCEPT = SET\_RPM * GAIN \quad (3)$$

RPM is the calculated RPM from equation (1), GAIN is a configurable gain identified during calibration of the drive mechanism 50, and SET_RPM is an RPM set point as determined by a user of the atherectomy system 10.

Once calculated or otherwise determined 108, the control signal 67 (e.g., Speed Control Signal or other control signal) may be outputted 110 to adjust and/or maintain a speed of the drive mechanism 50. In some cases, the calculated or determined control signal 67 may be outputted to a valve controlling a fluid of fluid to the drive mechanism 50 or directly to a drive mechanism to adjust a voltage or a current to the drive mechanism 50.

In some cases, the control signal 67 may be modified and/or determined by the damping control module 68 or other module or component of the firmware 62. In one example, the control signal may be modified and/or determined by following the method 200 depicted in FIG. 5, where the damping control module 68 may be configured to determine a control signal to adjust a speed to of the drive mechanism 50 during an in initial speed (e.g., RPM or other speed) overshoot, at steady state speed (e.g., RPM or other speed) oscillation, and/or at one or more other times during operation of the drive mechanism 50.

The method 200 may include determining 202 an initial control signal for controlling a speed of the drive mechanism 50. In some cases, the initial control signal for controlling the speed of the drive mechanism 50 may be determined 202 according to equation (2), but this is not required. The method 200 may further include determining 204 whether a predetermined period of time has elapsed. If the predetermined period of time has not elapsed, the method 200 may include adjusting 206 the initial control signal according to a first mode of operation (e.g., using the initial overshoot control 70, as discussed in greater detail below) to identify a determined control signal (e.g., the determined control signal 67 or other determined control signal). The determined control signal may be outputted 210 to a further component of the atherectomy system 10 to control a speed of the drive mechanism 50, as discussed herein. If the predetermined period of time has elapsed, the method 200 may include adjusting 208 the initial control signal according to a second mode of operation (e.g., using the steady state control 72, as discussed in greater detail below) to identify the determined controller signal (e.g., the determined control signal 67 or other determined control signal). The determined control signal may be outputted 210 to a further component of the atherectomy system 10 to control a speed of the drive mechanism, as discussed herein.

For use in the method 200 and/or other methods, the damping control module 68 may include the initial overshoot control 70 configured to calculate a control signal 67 according to an initial equation during a period of time associated with an initial speed overshoot mode of the drive mechanism 50 (e.g., according to the first mode of operation) and the steady state control 72 configured to calculate a control signal 67 according to a different equation for a steady state speed oscillation mode of the drive mechanism 50 (e.g., according to the second mode of operation) after the period of time associated with the initial speed overshoot mode has elapsed. Further, as an alternative to using different equations for determining the control signals 67 in the initial speed overshoot mode and the steady state speed oscillation mode, a single, time-dependent equation may be utilized or more than two equations may be utilized to determine the control signals 67 when in the initial speed overshoot mode and the steady state speed oscillation mode.

The period of time associated with the initial speed overshoot mode may be a suitable period of time upon startup of the drive mechanism 50 prior to the drive mechanism 50 reaching steady state operation relative to startup conditions. Example periods of time include, but are not limited to, five hundred (500) ms, one (1) second, two (2) seconds, and/or other periods of time.

Adjustments 206 to a control signal with the initial overshoot control 70 may depend on a flow cap equation, as follows:

$$\text{DAMP\_FLOWCAP} = (\text{RPM\_Y\_INTERCEPT} - \text{DAC\_COUNT\_SET\_RPM}) * \text{DampFactor} \quad (4)$$

RPM_Y_INTERCEPT is the value from equation (3), DAC_COUNT_SET_RPM is a digital to analog converter count for SET_RPM, and DampFactor is a configurable factor determined during calibration of the drive mechanism 50. The damping control module 68 may then compare a DAMP_FLOWCAP value from equation (4) to a RPM_Y_INTERCEPT value from equation (3).

If the RPM_Y_INTERCEPT value is equal to or less than the DAMP_FLOWCAP value, then the damping control module 68 may not modify the Speed Control Signal determined in equation (2). If the RPM_Y_INTERCEPT value is greater than the DAMP_FLOWCAP value, then the damping control module 68 may adjust the Speed Control signal of equation (2) to determine a dampened control signal 67 for initial overshoot, (Speed Control Signal)$_{dio}$, as follows:

$$(\text{Speed Control Signal})_{dio} = \text{Speed Control Signal} - (\text{DAMP\_FLOWCAP} - \text{RPM\_Y\_INTERCEPT}) \quad (5)$$

where the Speed Control Signal is determined from equation (2), the DAMP_FLOWCAP is determined from equation (4) and the RPM_Y_INTERCEPT is determined from equation (3).

Adjustments 208 to a control signal with steady state control 72 during operation of the drive mechanism 50 in the steady state speed oscillation mode may be based on a rate of change between a current determined speed of the drive mechanism 50 and a previous determined speed of the drive mechanism 50. An example rate of change equation is as follows:

$$\text{Rate of Change} = \text{Current Speed} - \text{Previous Speed} \quad (6)$$

The Current Speed may be the RPM value determined from equation 1 at an interval i, and the Previous Speed may be the RPM value determined from equation 1 at an interval i-n, where n is a number of intervals previous to the current interval, i. In some cases, the Previous Speed may be an average of, or other suitable statistic of, speeds determined using equation (1) for a set of previous intervals.

Using the Rate of Change value calculated from equation (6), the damping control module may determine a dampened rate of change as follows:

$$\text{DAMP\_RATE\_OF\_CHANGE} = \text{Rate of Change} * (\text{DampFactor})_{ss} \quad (7)$$

A value for Rate of Change may be determined from equation (6) and the (DampFactor)$_{ss}$ may be a fixed value assigned by the firmware 62. Based on the DAMP_RATE_OF_CHANGE value, the damping control module 68 may adjust the Speed Control signal of equation (2) to determine a dampened control signal for steady state, (Speed Control Signal)$_{dss}$, and maintain a stable speed after initial startup of the drive mechanism 50, as follows:

$$(\text{Speed Control Signal})_{dss} = \text{Speed Control Signal} - \text{DAMP\_RATE\_OF\_CHANGE} \quad (8)$$

where the Speed Control Signal is determined from equation (2) and the DAMP_RATE_OF_CHANGE is determined from equation (7).

As depicted in FIG. 3, the firmware 62 of the controller 56 may include a stall predictor control 74. In some cases, the stall predictor control 74 may be in and/or part of the damping control module 68 and/or separate from the damping control module 68.

The stall predictor control 74 may be configured to predict that a stall of the drive mechanism 50 is going to occur and/or when the stall is going to occur. In some, cases the stall predictor control 74 may be configured to follow a method 300 of determining if and when a stall will occur, as depicted in FIG. 6.

Figure 6:
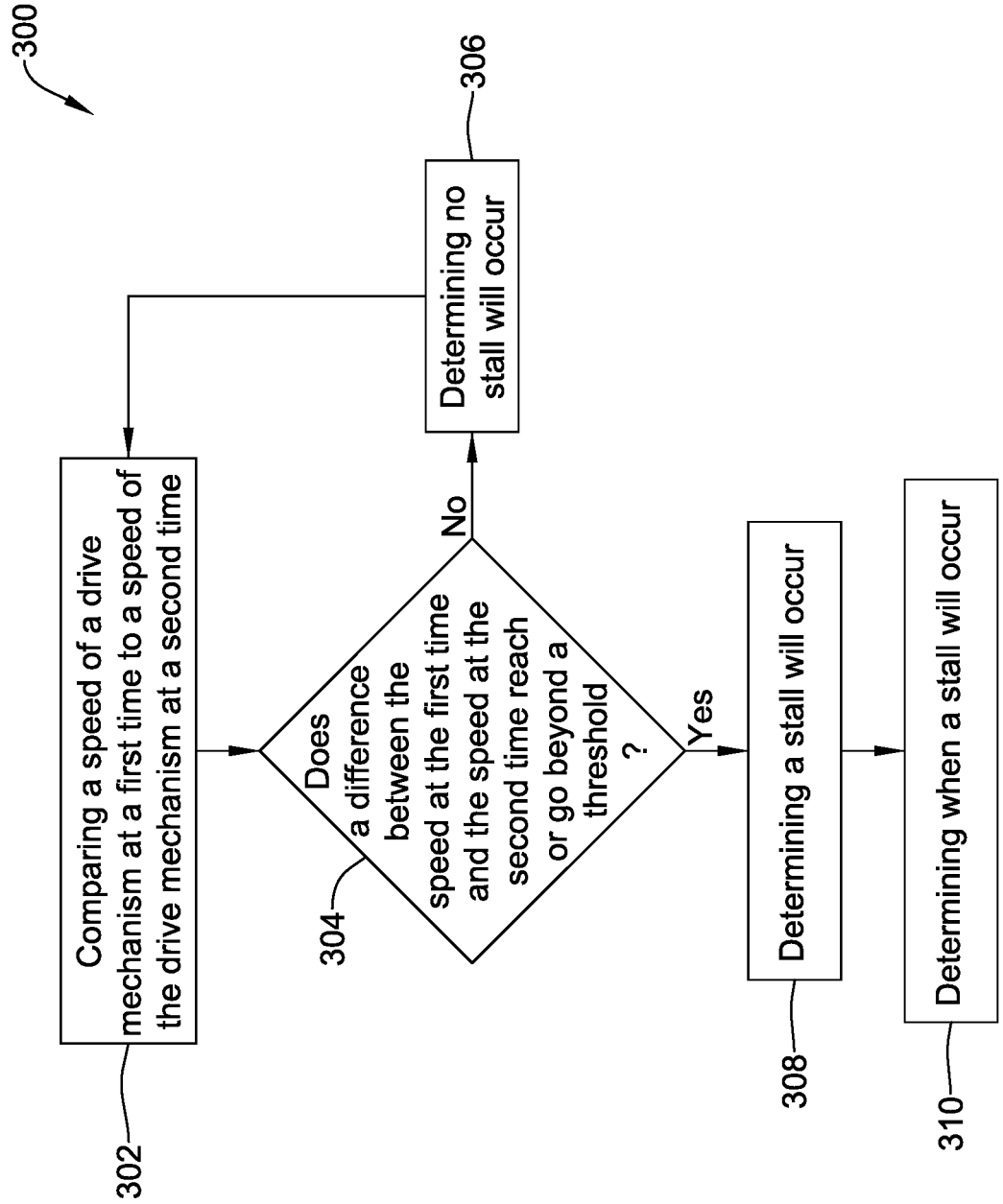
FIG. 6 depicts a schematic flow diagram of an example method of determining when a stall of a drive mechanism will occur.

As shown in FIG. 6, the method 300 may include comparing 302 a determined speed (RPM or other measurement of speed) of a drive mechanism 50 at a first time to a determined speed of the drive mechanism 50 at a second time. In some cases, the determined speeds at the first time and the second time may be determined according to equation (1) discussed above. Alternatively or in addition, speeds of the drive mechanism 50 may be determined in one or more other manners.

The first time and the second time at which the speed of the drive mechanism 50 are determined may be any suitable times during operation of the drive mechanism 50. In one example, the first time may be a current time such that the speed of the drive mechanism 50 determined at the first time is a current speed of the drive mechanism 50. In the example, the second time may be a period of time before the current time such that the speed of the drive mechanism 50 determined at the second time is a previous speed of the drive mechanism 50. An equation for comparing the speed of the drive mechanism 50 at a first time to a speed of the drive mechanism 50 at a second time is as follows:

$$\text{RPM deviation} = \text{RPM}_{i\text{-}t} - \text{RPM}_i \quad (9)$$

where $\text{RPM}_i$ is a speed of the drive mechanism 50 at a current time, i, $\text{RPM}_{i\text{-}t}$ is a speed of the drive mechanism 50 at a time of a predetermined period of time, t, before a current time, i, and RPM deviation (e.g., RPM deviation trend value) is a difference between the speed of the drive mechanism 50 at the predetermined period of time before a current time and the speed of the drive mechanism 50 at the current time. The speed at the predetermined period of time before a current time may be a single speed at the predetermined time before the current time, an average of a plurality of speeds at each of several intervals of periods of time prior to the current time, and/or other statistic related to speeds determined at times prior to the current time.

The period of time before the current time may be a predetermined period of time. Example predetermined periods of time may include fifty (50) ms, one hundred (100) ms, five hundred (500) ms, one (1) second, two (2) seconds, and/or other suitable predetermined period of time greater than and, optionally, a multiple of a period of time between determinations of a speed of the drive mechanism 50.

In the method 300, the difference (e.g., RPM deviation or RPM deviation trend value) between the speed of the drive mechanism 50 at the current time and the speed of the drive mechanism 50 at a predetermined period of time before the current time may be compared to a threshold value. A determination 304 may then be made as to whether the difference between the speed of the drive mechanism 50 at the first time and the speed of the drive mechanism 50 at the second time reaches or goes beyond a threshold. If the difference between the speed of the drive mechanism 50 at the first time and the speed of the drive mechanism 50 at the second time does not reach or go beyond the threshold, the stall predictor control 74 may determine 306 that no stall will occur between a current time and a time at which the next stall prediction is made (e.g., over a future time period equal to or substantially equal to the predetermined period of time). If the difference between the speed of the drive mechanism 50 at the first time and the speed of the drive mechanism 50 at the second time does reach or go beyond the threshold, the stall predictor control 74 may determine 308 that a stall will occur between a current time and a time at which the next stall prediction is made (e.g., over a future time period equal to or substantially equal to the predetermined period of time).

The threshold value may be any suitable threshold value. In one example and when using equation (9), the threshold value may be equal to zero (0), may be a number less than zero (0) and/or one or more other suitable values indicative of when a stall may be expected to occur.

When the stall predictor control 74 makes a determination 306, 308, the controller 56 may take one or more action to indicate the determination. In some cases, the one or more actions may be to enable or disable a stall indicator on a display screen (e.g., the display 30), enable or disable a light, enable or disable a sound, enable or disable a control signal for controlling the drive mechanism 50 to address the predicted stall or no-stall, and/or take one or more other actions or inactions.

When it has been predicted that a stall will occur, the method 300 may include determining 310 when the stall is predicted to occur. In some cases, a time at which the stall is predicted may be determined from the following equation:

$$\text{Predicted Stall Time} = ([\text{predetermined period of time}]/\text{RPM deviation})*(\text{RPM}_i - \text{RPM}_{stall}) \quad (10)$$

where the predetermined period of time is a time between the first time at which the speed of the drive mechanism 50 may be determined and the second time at which the speed of the drive mechanism 50 may be determined, RPM deviation is a difference between the speed of the drive mechanism 50 determined at the current time and the speed of the drive mechanism 50 determined at the predetermined time before the current time (e.g., as determined form equation (9)), $\text{RPM}_i$ is a speed of the drive mechanism 50 at the current time, i, and $\text{RPM}_{stall}$ is a threshold speed level at which the drive mechanism 50 is considered to be stalled.

Example threshold speed levels (e.g., $\text{RPM}_{stall}$) may include, but are not limited to, may be zero (0) RPM, one hundred (100) RPM, five hundred (500) RPM, one thousand (1,000) RPM, 1,500 RPM, 5,000 RPM, or other suitable threshold value. Additionally or alternatively, the threshold speed value may be a percentage of a set point speed or other motor parameter or state. In some case, the threshold speed value at which a stall may be considered to occur may be greater than zero (0) to facilitate recognizing a stall prior to the stall actually occurring.

Once the time at which the stall is predicted to occur has been determined (e.g., using the Predicted Stall Time from equation (10)), the controller 56 may take one or more actions. For example, the controller 56 may display on the display 30 the predicted time at which a stall may occur, sound an alarm, audibly indicate the predicted time at which a stall may occur, change operation of the drive mechanism in accordance with a control program, send an alert to the host 54, send an alert to a remote device or mobile device, and/or take one or more other actions.

Although not necessarily depicted in the FIGS., the methods described herein (e.g., methods 100, 200, 300, and/or other methods) may include one or more steps other than those steps described herein and/or the described steps may be performed in one or more other orders, as desired unless an expressly indicated otherwise. Moreover, the methods described herein may be repeated during operation of the atherectomy system 10 upon request or initiation, continuously, continuously at predetermined intervals, and/or at other times.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. An atherectomy system comprising:
a controller configured to configured to control rotation of a rotational device, the controller comprises:
a speed feedback module configured to receive a position indicator signal indicating a position of a drive mechanism; and
a speed compensation module, the speed compensation module including a damping control module; and
wherein the speed compensation module is configured to receive a speed of the drive mechanism from the speed feedback module and the damping control module is configured to determine a control signal based on the speed of the drive mechanism and output the control signal to control the drive mechanism.

2. The atherectomy system of claim 1, wherein the damping control module includes an initial overshoot control component configured to determine the control signal when the drive mechanism is in an initial speed overshoot mode.

3. The atherectomy system of claim 2, wherein the initial overshoot control component is configured to determine the control signal during a time period that is associated with the initial speed overshoot mode and spanning from a startup time of the drive mechanism to a set time after startup of the drive mechanism.

4. The atherectomy system of claim 1, wherein the damping control module includes a steady state control component configured to determine the control signal when the drive mechanism is in a steady state mode.

5. The atherectomy system of claim 4, wherein the steady state control component is configured to determine the control signal during a time period that is associated with the steady state mode and starting after a timer period that is that is associated with an initial speed overshoot mode of the drive mechanism has elapsed.

6. The atherectomy system of claim 1, wherein the damping control module includes:
an initial overshoot control component configured to determine the control signal when the drive mechanism is in an initial speed overshoot mode; and
a steady state control component configured to determine the control signal when the drive mechanism is in a steady state mode.

7. The atherectomy system of claim 1, wherein the damping control module includes a stall predictor control component configured to determine whether a stall of the drive mechanism is predicted to occur.

8. The atherectomy system of claim 7, wherein the stall predictor control component is configured to enable a control signal configured to address a predicted stall when the stall of the drive mechanism is predicted to occur.

9. The atherectomy system of claim 7, wherein the stall predictor control component is configured to predict a stall of the drive mechanism will occur within a predetermined time period after a current time when a trend value based on a speed of the drive mechanism reaches or goes beyond a threshold value.

10. The atherectomy system of claim 1, wherein the damping control module includes:
an initial overshoot control component configured to determine the control signal when the drive mechanism is in an initial speed overshoot mode;
a steady state control component configured to determine the control signal when the drive mechanism is in a steady state mode; and
a stall predictor control component configured to determine whether a stall of the drive mechanism is to occur based on current conditions.

11. A control system configured to control a rotational atherectomy device, comprising:
a controller configured to control rotation of a rotational device, the controller comprises a damping control module configured to receive a speed control signal for a drive mechanism and the damping control module includes:
an initial overshoot control component configured to determine a damping control signal based on the speed control signal when the drive mechanism is in an initial speed overshoot mode;
a steady state control component configured to determine the damping control signal based on the speed control signal when the drive mechanism is in a steady state mode; and
a stall predictor control component configured to determine whether a stall of the drive mechanism is predicted to occur.

12. The control system of claim 11, wherein the initial overshoot control component is configured to determine the damping control signal based on a value of a flow cap equation, the speed control signal, a speed set point for the drive mechanism, and a gain factor for the drive mechanism.

13. The control system of claim 12, wherein the initial overshoot control component is configured to:
compare a value of the flow cap equation to a product of the speed set point and the gain factor;
when the product of the speed set point and the gain factor is greater than the value of the flow cap equation, set the damping control signal as a value of:

(the speed control signal)−((value of the flow cap equation)−(the product of the speed set point and the gain factor))

when the product of the speed set point and the gain factor is less than or equal to the value of the flow cap equation, set the damping control signal to the speed control signal.

14. The control system of claim 11, wherein the steady state control component is configured to determine the damping control signal based on a rate of change of speed of the drive mechanism and the speed control signal.

15. The control system of claim 14, wherein the rate of change of speed of the drive mechanism is a dampened rate of change based on a damp factor value and a difference between a current speed of the drive mechanism and a previous speed of the drive mechanism.

16. The control system of claim 15, wherein the damping control signal is the speed control signal less the dampened rate of change.

17. The control system of claim 11, wherein the stall predictor control component is configured to predict a stall of the drive mechanism will occur within a predetermined time period after a current time when a trend value based on a speed of the drive mechanism reaches or goes beyond a threshold value.

18. The control system of claim 11, wherein when the stall predictor control component predicts a stall to occur, the stall predictor control component is configured to predict a time of the stall based on a time period between when a first speed of the drive mechanism is determined and when a second speed of the drive mechanism is determined, the first speed, the second speed, and a threshold speed level at which the drive mechanism is considered to be stalled.

19. A method of controlling a drive mechanism of an atherectomy system using firmware in a controller, the method comprising:
   determining an initial control signal based on a speed of the drive mechanism and a speed set point for the drive mechanism;
   during a predetermined time period after startup of the drive mechanism, adjusting the initial control signal according to a startup mode of operation to determine a damping control signal for the drive mechanism;
   after the predetermined time period after startup of the drive mechanism has elapsed, adjusting the initial control signal according to a steady state mode of operation to determine the damping control signal for the drive mechanism; and
   outputting the damping control signal to adjust the speed of the drive mechanism.

20. The method of claim 19, further comprising:
   predicting whether a stall of the drive mechanism will occur; and
   when a stall of the drive mechanism is predicted to occur, determining when the stall of the drive mechanism will occur.

* * * * *